United States Patent
Kühn et al.

(10) Patent No.: US 9,818,588 B2
(45) Date of Patent: Nov. 14, 2017

(54) METHOD AND ARRANGEMENT FOR THE CONTROL OF MEASURING SYSTEMS, CORRESPONDING COMPUTER PROGRAM AND CORRESPONDING COMPUTER-READABLE STORAGE MEDIUM

(75) Inventors: Andreas Kühn, Bremen (DE); Michael W. Linscheid, Berlin (DE); Katja Tham, Berlin (DE); Johann-Christoph Freytag, Kleinmachnow (DE); Stephan Werner Heymann, Berlin (DE)

(73) Assignee: Thermo Fisher Scientific (Bremen) GmbH, Bremen (DE)

( * ) Notice: Subject to any disclaimer, the term of this patent is extended or adjusted under 35 U.S.C. 154(b) by 1845 days.

(21) Appl. No.: 12/989,951

(22) PCT Filed: Apr. 28, 2009

(86) PCT No.: PCT/EP2009/003355
§ 371 (c)(1),
(2), (4) Date: Aug. 11, 2011

(87) PCT Pub. No.: WO2009/138207
PCT Pub. Date: Nov. 19, 2009

(65) Prior Publication Data
US 2012/0046872 A1    Feb. 23, 2012

(30) Foreign Application Priority Data
Apr. 28, 2008   (DE) .................. 10 2008 021 703

(51) Int. Cl.
*G01N 33/48*    (2006.01)
*H01J 49/00*    (2006.01)
*G06F 19/22*    (2011.01)
*G06G 7/58*     (2006.01)

(52) U.S. Cl.
CPC .......... *H01J 49/0031* (2013.01); *G06F 19/22* (2013.01); *H01J 49/0036* (2013.01)

(58) Field of Classification Search
CPC .......... G06F 19/18; G06F 19/22; G06F 19/24; G06F 19/32
See application file for complete search history.

(56) References Cited

U.S. PATENT DOCUMENTS

| | | |
|---|---|---|
| 2005/0063864 A1 | 3/2005 | Sano et al. |
| 2006/0043281 A1 | 3/2006 | Yoshinari et al. |
| 2006/0192101 A1 | 8/2006 | Takada et al. |
| 2007/0187588 A1 | 8/2007 | Yoshinari et al. |

*Primary Examiner* — Eric S Dejong
(74) *Attorney, Agent, or Firm* — David A. Schell; Charles B. Katz

(57) ABSTRACT

Disclosed herein is a method and an arrangement for the control of measuring systems such as a mass spectrometer or nuclear magnetic resonance (NMR) instrument, the control being based on an online data analysis of the current measurements. Depending on the measurement experiment, the combined result of the data analysis can have either a direct influence on the next measurement or result in a dynamically organized sequence of measurements. The measuring systems may be controlled by establishing a database that comprises information on the objects to be measured, the measurement data which can be detected during the measurement experiments using the measuring systems, and information regarding the relationships between or among items of the measurement data.

24 Claims, 8 Drawing Sheets

> L(NV)E(ELT)E(KAF)    700

SEQUENCE LISTING

<160> NUMBER OF SEQ ID NOS: 11

<210> SEQ ID NO 1
<211> LENGTH: 5
<212> TYPE: PRT
<213> ORGANISM: Homo sapiens

<400> SEQUENCE: 1

Arg Gln Lys Gly Lys
1               5

<210> SEQ ID NO 2
<211> LENGTH: 12
<212> TYPE: PRT
<213> ORGANISM: Homo sapiens

<400> SEQUENCE: 2

Arg His Pro Glu Tyr Ala Val Ser Val Leu Leu Arg
1               5                   10

<210> SEQ ID NO 3
<211> LENGTH: 7
<212> TYPE: PRT
<213> ORGANISM: Homo sapiens

<400> SEQUENCE: 3

Tyr Leu Tyr Glu Ile Ala Arg
1               5

<210> SEQ ID NO 4
<211> LENGTH: 15
<212> TYPE: PRT
<213> ORGANISM: Homo sapiens

<400> SEQUENCE: 4

Lys Val Pro Gln Val Ser Thr Pro Thr Leu Val Glu Val Ser Arg
1               5                   10                  15

<210> SEQ ID NO 5
<211> LENGTH: 14
<212> TYPE: PRT
<213> ORGANISM: Homo sapiens

<400> SEQUENCE: 5

Met Pro Cys Thr Glu Asp Tyr Leu Ser Leu Ile Leu Asn Arg
1               5                   10

<210> SEQ ID NO 6
<211> LENGTH: 10
<212> TYPE: PRT
<213> ORGANISM: Homo sapiens

<400> SEQUENCE: 6

Lys Gln Thr Ala Leu Val Glu Leu Leu Lys
1               5                   10

<210> SEQ ID NO 7
<211> LENGTH: 10
<212> TYPE: PRT
<213> ORGANISM: Homo sapiens

<400> SEQUENCE: 7

Leu Val Asn Glu Leu Thr Glu Phe Ala Lys
1               5                   10

```
<210> SEQ ID NO 8
<211> LENGTH: 11
<212> TYPE: PRT
<213> ORGANISM: Homo sapiens

<400> SEQUENCE: 8

His Pro Glu Tyr Ala Val Ser Val Leu Leu Arg
1               5                   10

<210> SEQ ID NO 9
<211> LENGTH: 11
<212> TYPE: PRT
<213> ORGANISM: Homo sapiens

<400> SEQUENCE: 9

His Leu Val Asp Glu Pro Gln Asn Leu Ile Lys
1               5                   10

<210> SEQ ID NO 10
<211> LENGTH: 14
<212> TYPE: PRT
<213> ORGANISM: Homo sapiens

<400> SEQUENCE: 10

Val Pro Gln Val Ser Thr Pro Thr Leu Val Glu Val Ser Arg
1               5                   10

<210> SEQ ID NO 11
<211> LENGTH: 20
<212> TYPE: PRT
<213> ORGANISM: Homo sapiens

<400> SEQUENCE: 11

Arg Asp Cys Lys Ser Thr Tyr Arg Lys Asp Arg Lys Phe Trp Leu Leu
1               5                   10                  15

Met Pro Ala Val
            20
```

METHOD AND ARRANGEMENT FOR THE CONTROL OF MEASURING SYSTEMS, CORRESPONDING COMPUTER PROGRAM AND CORRESPONDING COMPUTER-READABLE STORAGE MEDIUM

BACKGROUND OF THE INVENTION

The invention relates to a method and an arrangement for the control of measuring systems, and a corresponding computer program and a corresponding computer-readable storage medium, which can be used in particular for controlling measuring instruments automatically by target-oriented intervention in a measuring experiment, the control being based on an online data analysis of the current measurements in each case. Depending on the measuring experiment, a serial or parallel measurement strategy can be adopted, in which the combined result of the data analysis either has a direct influence on the next measurement or results in a dynamically organized sequence of measurements. The manner in which particular device parameters are altered as a function of the statement is established for a measuring experiment by means of the variation strategy. The measuring experiments can be, in particular, elucidation of monomer sequences of biopolymers by MS (mass spectrometry), elucidation of 3D molecular structure using NMR (nuclear magnetic resonance) or the like.

Analytes are analyzable, measurable substances that can be investigated with various kinds of measuring instruments with respect to their properties and their behavior. Properties and behavior of analytes are covered hereinafter by the general term properties.

Based on measurement data from measuring experiments, which possess a defined measuring arrangement and execution, results can be derived and can be combined in the sense of the evaluation strategy used and can be interpreted as statements about analytes of interest.

If there is a time-dependent variation of analytes or analyte compositions in measuring arrangements, then time windows arise, in which particular measurement data are accessible. These arrangements are termed time-critical measuring experiments hereinafter.

The amount of all derivable results of a measuring experiment, which are combinable in the sense of the evaluation strategy, is designated hereinafter as the overall statement and is used for answering a given formulated question (definition of a "formulated question" will be given later). We want to find the amount of derivable, combined individual results (statements) that can be linked together into an overall statement and which answer the formulated question unambiguously and completely.

For automating measuring experiments, at present methods are used that are characterized by rigid measurement sequences. Each measurement is based on an established set of instrument parameters, which predetermines the measuring mode of the system.

These measuring modes can either be defined beforehand or can be determined based on current measurement data and resultant data relations for the continuation of measurement. However, the course of measurement can only be influenced to a very limited extent, because until now only measurement data and data relations between these directly derivable from the measurement are used as indicators, in order to initiate previously defined measurements. However, these indicators are not sufficient on their own for extracting statements with respect to a more complex formulation of a question.

Up until now, evaluation has been carried out in a processing step following the test run. If the question formulated beforehand cannot be answered with the results that are derivable herein and are combinable in the sense of the chosen evaluation strategy (overall statement), further measuring experiments are necessary possibly with altered measuring modes. This principle results in a serial sequence of test runs and processing steps until answering is possible or no further measurements can be performed. This process can sometimes be very time-consuming, as an evaluation that is always downstream only permits the target-oriented change of particular measuring modes after completion of an entire experiment. This leads to increased consumption of metrological resources and a possibly limited amount of analytes to be investigated. In addition it results in large amounts of redundant data.

SUMMARY OF THE INVENTION

The task of the present invention therefore consists of providing a method and an arrangement for the control of measuring systems, and a corresponding computer program and a corresponding computer-readable storage medium, which avoid the disadvantages of the known solutions and in particular make it possible to evaluate complex relations between measurement data and, on the basis of the derived evaluation results and/or statements derived and interpreted therefrom during the course of a measuring experiment, to intervene in the measuring experiment in a target-oriented manner.

The invention described can preferably be used in cases where the following criteria/conditions are fulfilled.

I. The measuring instruments used possess device parameters that can be varied via a control module and whose respective influence on the measurement is or can be defined. Moreover the measuring instruments possess a measured data module for output of the measured values obtained in a measurement.

II. A formulated question that is being examined is in principle to be answered with a measuring experiment on the measuring instruments used or is unambiguously soluble. Possible formulated questions are for example a) the elucidation of properties and behavior of the measurement objects under examination based on the measured values that arise, b) the elucidation of effects of device parameters and combinations thereof on measurement data and resultant relations, c) finding device parameters and/or sets of device parameters for which a defined amount of measurement data and/or a defined amount of data relations occur and d) any combination of a)-c).

III. For solving the formulated question or partial formulated questions there is in each case at least one evaluation strategy that defines the statements required for the solution, such as for example information on properties and the behavior of measurement objects and the procedure for combining these from partial statements, such as for example information about partial properties. If all required partial statements or information on partial properties are to be determined unambiguously and completely, then the solution of the formulated question or partial formulated questions is also complete and unambiguous.

IV. All theoretically arising measurement data and all data relations constructable therefrom of the measurement objects to be investigated, can be generated computationally and combinatorially and can be linked with statements in each case derivable therefrom, such as for example information on (partial) properties of the measurement objects under examination. Additional information (not generable by the measuring system) can also be incorporated, and the underlying data relations can be almost arbitrarily complex and almost arbitrarily extensive. The part of statements or information relevant to the formulated question forms, coupled with the corresponding/underlying measurement data and data relations, the database, which is produced before the measuring experiment.

V. Simple data requests for measurement data and data relations to this database produce the required statements, such as for example information on partial properties and optionally related statements. The resultant speed advantage against the previously used computational-combinatorial approach (production) then makes it possible to determine statements or information on properties of the measurement objects to be investigated, which are not otherwise accessible at run time (contemporaneously).

VI. Directly after a measurement has been evaluated, it is possible to determine whether a statement, such as for example the information about a property, could be determined unambiguously and completely or which partial statements or partial properties could only be determined ambiguously or incompletely.

VII. The statements relating to the same formulated question, for example the information about partial properties relating to the same property of a particular measurement object can be composed from different measurements/evaluations, so as to be made complete and unambiguous.

VIII. For a measuring experiment, a measuring system-specific variation strategy is established, which depending on the formulated question either for a) in the case of nonunambiguous and incomplete determinable information alters partial properties from the evaluation of a measurement, the device parameters are altered in such a way that "it is to be expected", that a) in the case of incomplete information about partial properties, what is still missing can be acquired and b) in the case of nonunambiguous determination, the missing information can be acquired, that is required about the underlying partial properties.

for b) determines how an examined device parameter or a set of device parameters under examination is varied, in order to capture the relative change of all arising measurement data and data relations.

for c) determines how an examined device parameter or the set of device parameters is varied systematically, so as to compare the measurement data resulting in each case with the required amount of measurement data/data relations.

IX. For carrying out a measuring experiment, a measurement strategy is established, which defines the procedure for applying the aforementioned variation strategies (of the device parameters). Depending on the desired or conditional focus, the variation can
a) take place in direct form. The device parameters of the next measurement are established on the basis of the current measurement. The measurement and evaluation sequence is then serial (measurement-evaluation-measurement-evaluation), b) in indirect/delayed form. Each evaluation conditions the input of a measurement with altered device parameters in a (tasks) measurement list, which is worked through. The measurement and evaluation sequence is then parallel.

This task is solved according to the invention by the features in the characterizing part of claims 1, 26, 29 to 30 in conjunction with the features in the introductory clause. Desirable embodiments of the invention are contained in the subclaims.

A special advantage of the method according to the invention is that time-critical measuring experiments, such as for example elucidation of amino acid sequences in biopolymers by mass spectrometry, can be influenced during the run time of the measuring experiment on the basis of measurement data, which were obtained during this measuring experiment. This is achieved according to the invention in that a database is provided that comprises at least a proportion of the measurement data obtainable during execution of a measuring experiment and/or at least a proportion of the information derivable from the measurement data that can be obtained. This information can preferably be relations between obtainable measurement data, such as for example differences between pairs of measurement data. Preferably the database stores data representing a large proportion of the result space, preferably the total result space, of the measurement data that can be recorded in the measuring experiment. Furthermore, the database can comprise further information about chemical and/or physical properties of the measurement objects and about relations between measured values (data relations), which can also be evaluated when a request is made to the database.

A preferred embodiment of the invention envisages that the measuring experiment is elucidation of amino acid sequences of biopolymers, in particular of peptides/proteins, by mass spectrometry (MS) or elucidation of 3D molecular structures by nuclear magnetic resonance (NMR), in this case the measurement objects to be measured can be biopolymers and/or their derivatives and/or the measurement data can be information about the mass of amino acids or amino acid sequences, about mass/charge ratios and/or signal intensity. Several monomers joined together in a chain form a polymer, and several monomers and/or polymers form a polymer or a derivative of a polymer or subunits thereof. Hereinafter, monomers, biopolymers or derivatives also mean modified monomers, modified biopolymers or modified derivatives. In particular, the biopolymers or derivatives can be proteins, peptides, DNA, RNA, PNA, LNA, TNA, GNA, polysaccharides, such as starch, cellulose or glycogen; lipids, polyglucosamines, such as chitin or chitosan; polyhydroxyalkanoates, cutin, suberin or lignin or combinations thereof.

The information about relations between obtainable measurement data can for example be differences between measurement data, in particular mass differences. In a preferred embodiment of the invention the database comprises mass differences in each case between two monomers and/or polymers of the biopolymers. Preferably the database also comprises mass differences between polymers, where the polymers differ by several monomers.

Along with information about attainable measurement data or relations between the measurement data, the database provided can further comprise information about at least a proportion of the measurement objects to be measured or also information about measuring experiments that have already been performed.

According to the invention, while the measuring experiment is running, the currently acquired measurement data are evaluated automatically, with the evaluation comprising the determination of relations between at least a proportion of the acquired measurement data. Based on the relations determined, the database is then interrogated, to obtain information about acquired measurement objects. The relations determined then serve at least partly as inquiry parameters. In a preferred embodiment of the invention, an inquiry takes place, where at least a proportion of the mass of biopolymer fragments of a fragment spectrum and at least a proportion of the mass differences between the biopolymer fragments serve as inquiry parameters. In a preferred embodiment of the invention, as a result of the inquiry, possible candidates for unelucidated parts of the sequence of the biopolymers, which arise during a mass spectrometric fragmentation, are determined.

In the database, information about relations between the measurement data is linked to further information about measurement objects that are to be measured. Depending on an evaluation strategy for the measuring experiment and depending on the information about acquired measurement objects that are identified by the inquiry parameters, control of the measuring instruments is now performed.

In a preferred embodiment of the invention it is envisaged that the data relations are constructed in the form of a table or a, possibly multidimensional, matrix. The table and/or matrix entries correspond in a preferred embodiment to the relations found between measurement data, such as for example mass differences, and the rows and/or columns relate to measurement objects. A preferred embodiment envisages that elements of a matrix correspond in each case to a mass difference, which are assigned to those polymers and/or polymer fragments whose masses differ by this mass difference, and which are for example assigned to the rows or columns in which the mass difference was entered. The masses of these (bio-)polymers and/or (bio-)polymer fragments would then be assigned to one another. As the result of the inquiry, information on assignment is generated, which for example comprises information about which (bio-)polymer fragments differ by the mass difference. The mass difference located in the matrix would then correspond to the difference of the masses of the two assigned (bio-)polymer fragments. Furthermore, the information on assignment can comprise information on the monomer or the polymer fragment, by which the two assigned (bio-)polymer fragments differ.

In a preferred embodiment of the invention these assignments are used for determining possible candidates for unelucidated sequence parts, using methods of graph theory, methods of artificial intelligence, e.g. fuzzy logic (neural network, genetic algo and/or evolution strategies etc.). In a preferred embodiment of the invention, an undirected graph is constructed for this, wherein it is produced in nodes for each mass determined by the inquiry. Between nodes, i.e. masses, which were assigned to a mass difference of the inquiry, an edge is defined.

In a preferred embodiment of the invention, graph-theory approaches are employed for determining possible candidates for unelucidated sequence parts. Along the edges, linking chains (paths) are produced starting from a mass, in the direction of increasing or decreasing mass. Preferably, formation of the linking chains is begun at the node with the lowest mass. Then all linking chains are determined, which run along the edges to nodes of ever higher mass until the node with the highest mass is reached. Formation of the linking chains can naturally also begin from the node with the highest mass in the decreasing direction until the node with the smallest mass is reached. The nodes within a connecting chain are also designated hereinafter as elements, the edges within a connecting chain as linkages. The edges are preferably assigned information about one or more monomers, which represent the mass difference between the two nodes (masses) linked by the edge. Possible candidates for unelucidated sequence parts of the biopolymers are then indicated if two masses are connected by an edge, which differ by a mass difference of more than one monomer:

The presence of unelucidated sequence parts is therefore indicated by the existence of linkages (edges) between elements (nodes) of the linking chain, to which mass differences are assigned, which correspond at least to the mass difference of two monomers, or if the lowest mass does not correspond to the mass of an individual monomer, or the mass difference of the highest mass corresponds to the unfragmented biopolymer of exactly two monomers. Conversely, the complete elucidation of the sequence of a biopolymer is indicated by a linking chain, whose linkages (edges) represent exclusively the mass of an individual polymer.

Depending on the available device parameters (for example fragmentation methods and corresponding parameters) and the expected effects of all parameters, a variation strategy is established for the possible statements of the formulated question (for example incomplete/non-unambiguous sequence coverage). If for example an unelucidated sequence part is determined, it is defined which (individual) statements have contributed to this. Now a) a fragment (with corresponding mass) can be selected, which contains this unelucidated sequence part. If there are several candidates, the one is selected that has sufficiently high intensity to be used for another fragmentation and contains as few known sequence parts as possible. Moreover, b) one or more parameters can be altered, so that there should for example be greater fragmentation (specialized knowledge about the method or evaluation by DBnovo) or c) another fragmentation method can be selected, which should provide complementary/additional information (for example side chain fragmentation) (specialized knowledge about the method or evaluation by DBnovo).

If it is necessary or advantageous to make the directly subsequent measurement dependent on the statement of the current measurement, a serial measurement strategy is followed. Here, measurement and corresponding evaluation are alternated continually. A derivable statement can then lead contemporaneously to a decision/intervention in the course of measurement. The time required for the evaluation may possibly have an adverse effect on the possible measurement density.

If a high measurement density is required, a parallel measurement strategy is followed, i.e. the instrument performs one measurement after another, without delays caused by evaluation. The evaluations are carried out in parallel with the measurements, and they result, through their statement and the established variation strategy, in new measurements. These measurements are then managed dynamically in a measurement list. The measurement list is worked through successively and can, for example by estimating the availability times, by complete elucidation or by other prioritization criteria of measurement objects, be altered in its sequence and extent. Time-critical measuring experiments can then sometimes even be organized and controlled more efficiently with respect to time.

An arrangement according to the invention has at least one chip and/or processor, the arrangement being set up in such a way that a method for controlling measuring systems can be executed, wherein a database is provided, which comprises information about at least a proportion of the measurement objects to be measured, about at least a proportion of the measurement data that can be recorded by the measuring experiments performed with the measuring system, and information about relations between at least a proportion of the measurement data. During the temporal course of a measuring experiment acquired measurement data are evaluated automatically, the evaluation comprising a determination of relations between at least a proportion of the acquired measurement data;
  at least one inquiry is made to the database, in order to obtain, by means of the relations determined, information about acquired measurement objects; and
  the measuring instruments are controlled in relation to the information about acquired measurement objects.

In the preferred embodiment from the area of mass spectrometry, the measuring system is preferably a mass spectrometer. A database in this case preferably comprises, among other things, mass differences between monomers and/or polymers of the biopolymers, and also in particular mass differences between polymers that differ by one or more monomers. When the database is interrogated, candidates can be determined for sequence parts of the biopolymers that have not yet been elucidated, these being indicated for example by mass differences of several monomers. Based on these determined but not yet elucidated sequence parts, the device parameters, such as for example supplied energy pulses, can be controlled.

A computer program for controlling the measuring instrument makes it possible for a data processing device, after it has been loaded in the memory of the data processing device, to carry out a method of control of measuring systems, wherein a database is provided, comprising information about at least a proportion of the measurement objects to be measured, about at least a proportion of the measurement data that can be acquired by the measuring experiments that are performed with the measuring system, and comprising information about relations between at least a proportion of the measurement data; during the temporal course of a measuring experiment acquired measurement data are evaluated automatically, the evaluation comprising a determination of relations between at least a proportion of the acquired measurement data;
  at least one inquiry is made to the database, in order to obtain, by means of the relations determined, information about acquired measurement objects; and
  the measuring system is controlled according to the information about acquired measurement objects.

In another preferred embodiment of the invention it is envisaged that the computer program according to the invention is of modular construction, with individual modules being installed on various data processing devices.

Advantageous embodiments additionally envisage computer programs by which further steps of the method or sequences of the method stated in the description can be carried out.

Such computer programs can for example be made available (for a fee or free of charge, freely accessible or password-protected) downloadable in a data or communication network. The computer programs thus provided can then be made usable by a method in which a computer program according to claim 29 is downloaded from an electronic data network, such as for example from the Internet, to a data processing device connected to the data network.

In order to carry out the method according to the invention for control of measuring systems, it is envisaged to use a computer-readable storage medium, on which a program is stored, which makes it possible for a data processing device, after it has been loaded into the memory of the data processing device, to carry out a method of control of measuring systems, wherein a database is provided, comprising information about at least a proportion of the measurement objects to be measured, about at least a proportion of the measurement data that can be acquired by the measuring experiments that are performed with the measuring system, and comprising information about relations between at least a proportion of the measurement data;

during the temporal course of a measuring experiment
  acquired measurement data are evaluated automatically, the evaluation comprising a determination of relations between at least a proportion of the acquired measurement data;
  at least one inquiry is made to the database, in order to obtain, by means of the relations determined, information about acquired measurement objects; and
  the measuring system is controlled according to the information about acquired measurement objects.

A particular advantage of the present invention comprises a rapid evaluation of mass spectra with respect to a question that has been formulated, with the possibility of targeted alteration of the current course of measurement. This opens up a large field of application in mass spectrometry.

It is possible to perform series of investigations on fragmentation mechanisms, in which several fragmentation parameters for particular amino acid sequences are varied systematically. The resulting changes are derivable and evaluable directly at run time. Statements can be tracked and documented in a targeted way.
  Device parameters can be optimized for particular amino acid sequences based on resultant mass spectra.
  Novel fragmentation reactions and methods can be optimized for the use of targeted, regiospecific bond cleavages. This could be utilized for successive fragmentation of large biomolecules on various binding sites (amino acid sequences), in order to obtain a complete sequencing from the resultant overlapping fragments.

BRIEF DESCRIPTION OF THE DRAWINGS

The invention will be explained in more detail below for an example, referring to the drawings, which show.

MS overview scan (A) and subsequent fragmentation of the three most intense peaks by IRMPD; MS2(IRMPD464.25) (B), MS2(IRMPD653.36) (C), MS2(IRMPD585.02) (D), FIG. 5 Example of elucidation of amino acid sequences in biopolymers: Illustration of the determination of masses from measurement data in an evaluation of fragment spectra, FIG. 6 As an example of elucidation of amino acid sequences in biopolymers: Illustration of the production of a matrix from mass differences, FIG. 7a As an example of elucidation of amino acid sequences in biopolymers: Illustration of the construction of a graph from results of a measurement request, FIG. 7b Example of elucidation of amino acid sequences in biopolymers: Abstracted illustration of the DBnovo evaluation method for preparation of statements from the measurement data of a measurement, FIG. 8 As an example of elucidation of amino acid sequences in biopolymers: Schematic illustration of an example of determination of paths in a graph, FIG. 9a Example of elucidation of amino acid sequences in biopolymers: Extracted ion traces of three peptides from an HPLC/MS measuring experiment, FIGS. 9b-d Example of elucidation of amino acid sequences in biopolymers: The increase in sequence coverage after altered measuring modes is shown for each peptide. In total, 10 measurements are required to identify the three peptides unambiguously. The difference from the previously required measurements (45 scans) can be utilized for the identification of additional peptides occurring in this time window.

Figure 10:
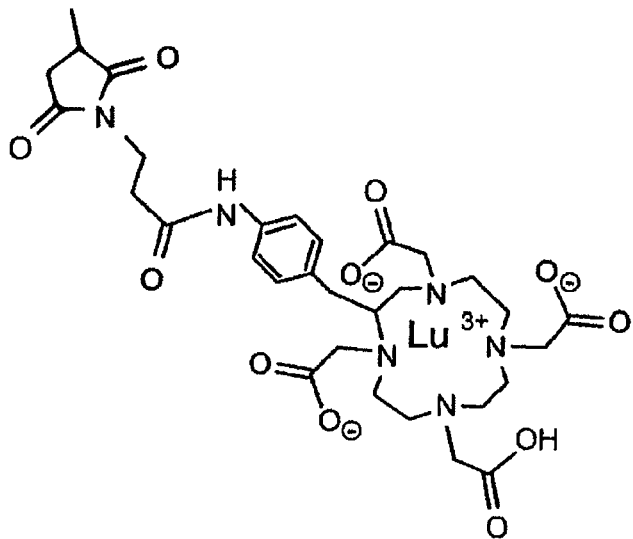
Figure 11:
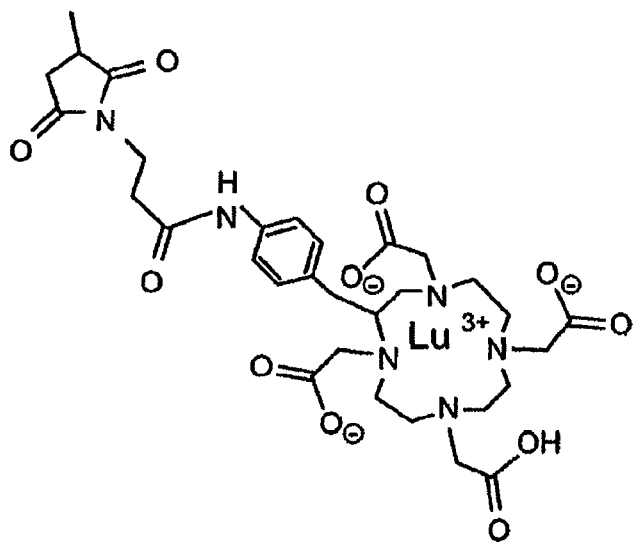

FIG. 10 Example of elucidation of amino acid sequences in biopolymers: Illustration of an evaluation of a fragment spectrum when using a first fragmentation mode and FIG. 11 Example of elucidation of amino acid sequences in biopolymers: Illustration of an evaluation of a fragment spectrum when using a second fragmentation mode.

DETAILED DESCRIPTION OF EMBODIMENTS OF INVENTION

In the following, the invention will be explained in more detail with an example of elucidation of amino acid sequences in biopolymers. The invention is not of course restricted to this particular example of embodiment, but also covers other measuring operations, for example structural elucidations such as elucidation of the 3D molecular structure or similar, provided only that the features defined in the independent claims are realized.

Brief Synoptic Description of the Invention:

The invention described here comprises an automated system for controlling measuring instruments, which is based on the online data analysis of the current measurements in each case, for target-oriented intervention in the measuring experiment.

Existing approaches only use measurement data and data relations between these derivable directly from the measurement as indicators, for initiating previously defined measurements. However, these indicators alone are insufficient for extracting statements with respect to a more complex formulated question from results that are derivable and linked in the sense of the evaluation strategy. As well as additional references to already known analyte information, references are also required that have been formed on the basis of simpler and/or on the basis of other relations.

In a measuring experiment, the current measurement in each case is evaluated in such a way that (partial) questions can be answered by statements derivable from the measurement data (in the form of interpreted results and results combined in the sense of the evaluation strategy). The derivation of these statements requires a particular evaluation strategy depending on the type of formulated question and the measuring mode used, sometimes being of very complex form and based on the generation of a variable large number of data relations. In order to obtain statements at run time and intervene in the course of measurement, provided the measurement is still current, i.e. before there is a change in analytes or analyte composition, a rapid method is required for evaluating the data relations.

Depending on the amounts of data arising and the existing complexity of evaluation, a computational algorithm can be very time-consuming and may be unsuitable especially in time-critical measuring experiments. However, if for a measuring experiment all possibilities that arise, i.e. all constructable data relations from all theoretical measured values of the analytes and/or analyte composition to be investigated can be generated computationally and combinatorially, then the complete result space of the evaluation or a part thereof selected for the measuring experiment can be represented by a database. This links individual data relations of the generated result space to information about measurement objects, their properties and/or data relations within the latter. The generated data relations of each measurement can therefore be evaluated by simple data requests to a database that can be generated before the experiment. (This is valid for a set of measuring experiments/particular measuring arrangement).

The invention presented here makes use of the speed of such data requests, and thus offers the possibility of real-time feedback of the derived statements to the next measurement run. This means that the manner in which the control of measurement is influenced at run time can be automated and can also be target-oriented with respect to complex (partial) formulated questions.

The present invention for automated and target-oriented measuring instrument control is applicable in particular, though not exclusively, for the following scenarios with corresponding formulated questions and goals:

Scenario 1:
  Answering questions relating to analyte properties
  Example: The elucidation of amino acid sequences of peptides/proteins by MS (mass spectrometry)
  The efficiency of measuring experiments can be increased with respect to the completeness and uniqueness of the amino acid sequences of peptides/proteins, in that after each measurement a statement about structure/sequence elucidation is available and based on unresolved structure/sequence parts, a targeted adjustment of the device parameters—at run time—is performed.
  Compared with existing approaches, either the number of measurements required for elucidating the amino acid sequences can be greatly reduced or the information content of the sequence information can be greatly increased.

Scenario 2:
  Elucidation of the influence/interrelations of individual or coupled device parameters on the measurement result obtained
  How, for example, does the fragmentation behavior of a group of biopolymers change, if the time between two supplied energy pulses is altered?
  By detecting all possible fragment parts and the accompanying changes in intensity of these fragments with change of the device parameters, it is possible to determine any regeoselectivity and sequence specificity that arise. An investigation that brings about a change of the device parameters is possible. Differentiation of whether an effect is intensified or attenuated with increase or decrease of the parameter is determinable. When there is variation of the parameter, this can be used for the evaluation, in order to ignore regions in which an effect is no longer to be noted. "Tuning" of parameters is therefore also possible when using several parameters. New instrument options/measuring methods can therefore be made usable for certain applications and can be optimized for basic functionality. Results from this application can be used for defining standard parameters or parameters for specific cases.

Scenario 3:
Optimization of device parameters (sets of parameters), in order to obtain a defined measurement result
Example: A particular set of device parameters is required for an instrument, giving cleavage of an analyte at a desired/specified position.

As in scenario 2, device parameters and sets of device parameters can be varied, in order to determine their influence on the measurement, for example the fragmentation efficiency. If the effects of the device parameters used can only be estimated with difficulty, especially when there is a large number of possible combinations between simultaneously used device parameters of the fragmentation methods, they can be optimized for a desired influence. If we are looking for the optimum sets of parameters for obtaining a favored bond cleavage, then it is possible to analyze, by systematic variation, when the specific fragments for this occur in larger quantity, without undesirable fragments being produced. It is also possible to assess the directions in which the parameters should be varied, in order to approach this goal. Results from this application can be used for defining standard parameters or parameters for specific cases.

Figure 1:
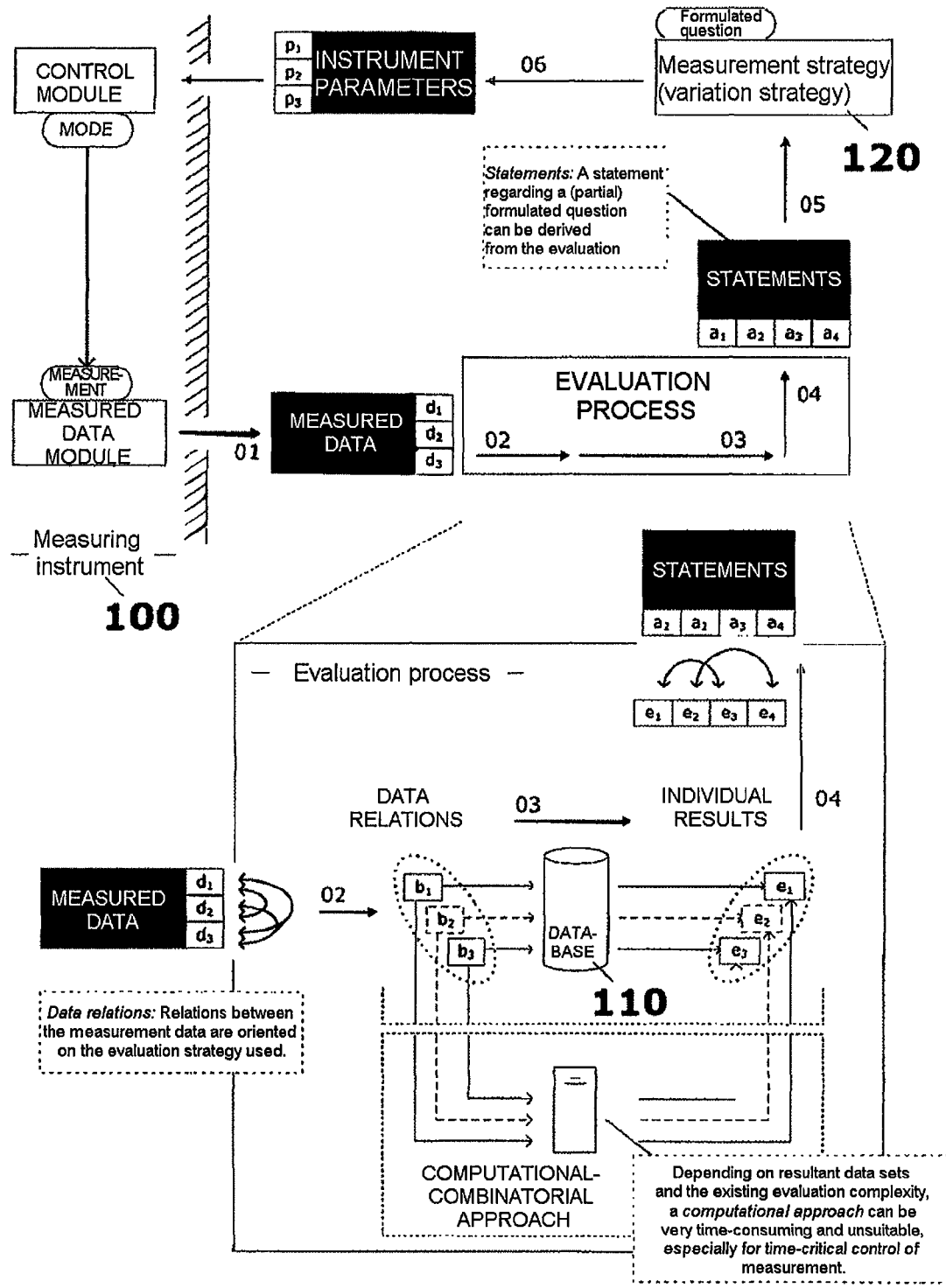
FIG. 1 Sketch of an automated and target-oriented measuring instrument control system based on a database-supported online data analysis and real-time feedback of resultant measurement results, FIG. 2 Example of elucidation of amino acid sequences in biopolymers: Fragment of the various series (a, b, c series (with N-terminus) and x, y, z series (with C-terminus)) for the example of the pentapeptide SEQ ID NO:1, FIG. 3 Example of elucidation of amino acid sequences in biopolymers: Temporal ion intensity curve of a set of peptides in the mass spectrometer (MS) with preceding separation system (HPLC), FIG. 4 Example of elucidation of amino acid sequences in biopolymers: Illustration of a rigid measurement sequence.

An example of automated, target-oriented control of a measuring instrument 100 will be described below, referring to FIG. 1.

Preparation of the measured values and deconvolution thereof take place in step 01. Step 01 comprises in particular the preparation of the measured values from the current measurement into processable measurement data $d_1$, $d_2$, $d_3$. This step can already be performed in parts by the measuring instrument 100.

Step 02 comprises generating the data relations. In this, relations are produced between the resultant measurement data $d_1$, $d_2$, $d_3$, resulting in data relations $b_1$, $b_2$, $b_3$. The nature of the data relations $b_1$, $b_2$, $b_3$ is determined by the chosen evaluation strategy. In an example of an embodiment from the area of mass spectrometry, the measurement data $d_1$, $d_2$, $d_3$ are mass values of biopolymers, in this case amino acids or amino acid sequences, which are related to one another by finding the differences between at least a proportion of the mass values.

Step 03, evaluation of the data relations $b_1$, $b_2$, $b_3$, serves for evaluating the data relations $b_1$, $b_2$, $b_3$ with the aid of directly executed online data requests to an existing or previously calculated database 110.

In step 04, statements $a_1$, $a_2$, $a_3$ are derived. For this, the individual results $e_1$, $e_2$, $e_3$, are derived and combined in such a way that statements $a_1$, $a_2$, $a_3$ can be found for answering (partial) questions. The tracking of these statements $a_1$, $a_2$, $a_3$ requires a particular evaluation strategy depending on how the question is formulated, and is based on the previously produced data relations $b_1$, $b_2$, $b_3$ and their linkages within the database. For the example mentioned of mass spectrometry, a formulated question may for instance relate to sequence regions that have not yet been elucidated. If these unelucidated sequence regions are found, say by determining mass differences, which indicate a sequence of at least two amino acids, a statement $a_1$, $a_2$, $a_3$ derived from the combined individual results can for example comprise stating these unelucidated sequence regions.

In step 05, the statements $a_1$, $a_2$, $a_3$ are compared with the question that is to be achieved. From the evaluation, a derived statement $a_1$, $a_2$, $a_3$ can be derived with respect to a (partial) formulated question. Step 05 is used for coordinating the extracted statements $a_1$, $a_2$, $a_3$ with the set of established partial questions (>target), with the aim of subsequent identification of strategies for continuing the measurement or for varying the device parameters.

In step 06, target-oriented variation of the device parameters $p_1$, $p_2$, $p_3$ takes place, i.e. the derived statements $a_1$, $a_2$, $a_3$ extracted from the current measured values flow directly (by essentially real-time feedback) into the next measurements of the experiment. (see generally: Variation strategy)

Application: Mass Spectrometry
Database-supported Online De-novo Sequencing of Biopolymers A possible application of the invention described here is the database-supported online-identification of biopolymers (e.g. peptides, proteins, DNA, RNA) using mass spectrometry and target-oriented control of the mass spectrometer.

Mass spectrometry is used in proteome research for elucidating (identifying) primary structures of proteins and peptides, i.e. their amino acid sequences and any modifications that have occurred.

The mass spectrometers used detect mass/charge ratios of the biopolymers being investigated, which are present in ionized forms (ions for short). Each measurement results in a mass spectrum, which compares the mass/charge ratio with the intensity. The resultant Gaussian distributions of the measurement data relating to the ions are called peaks hereinafter. From the distances between the peaks, charges can be determined, from which the masses (m) of the peptides are calculated (deconvolution).

Figure 2:
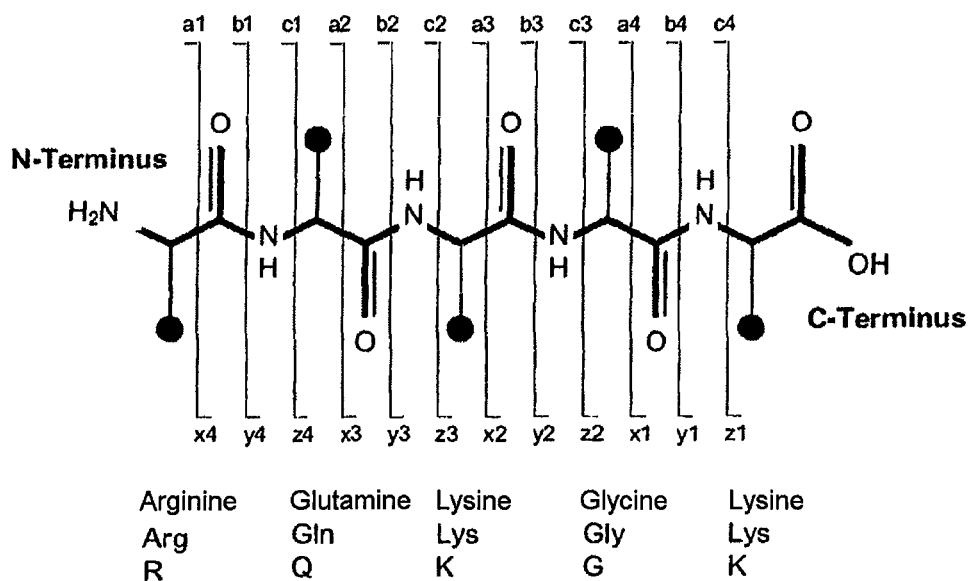

Once all peptide masses have been determined in an overview mass spectrum (MS), in the next step peptide ions are selected and fragmented into smaller fragments for structure elucidation (tandem mass spectrometry, MSn). This results in fragment spectra, in which—depending on the fragmentation method used (CID=Electron Capture Dissociation, IRMPD=Infrared Multiphoton Dissociation, ECD=Collision Induced Dissociation)—specific fragments of the selected precursor ion (peptide) can be observed. These can be divided into various series (a, b, c series or x, y, z series). The various series are presented synoptically in FIG. 2 for the example of the pentapeptide SEQ ID NO:1 and formally are formed by successive and series-specific cleavage of the individual amino acids starting from one end of the peptide (C/N-terminus). Depending on the fragmentation efficiency and hence on parameters such as the normalized collision energy (in CID), laser performance (in IRMPD) or the duration and delay of the effects of electrons (ECD), there is a varying level of coverage of the observable fragment series. Depending on the completeness and overlaps of the fragment series, the complete and unambiguous sequence of the amino acids can be determined.

Figure 3:
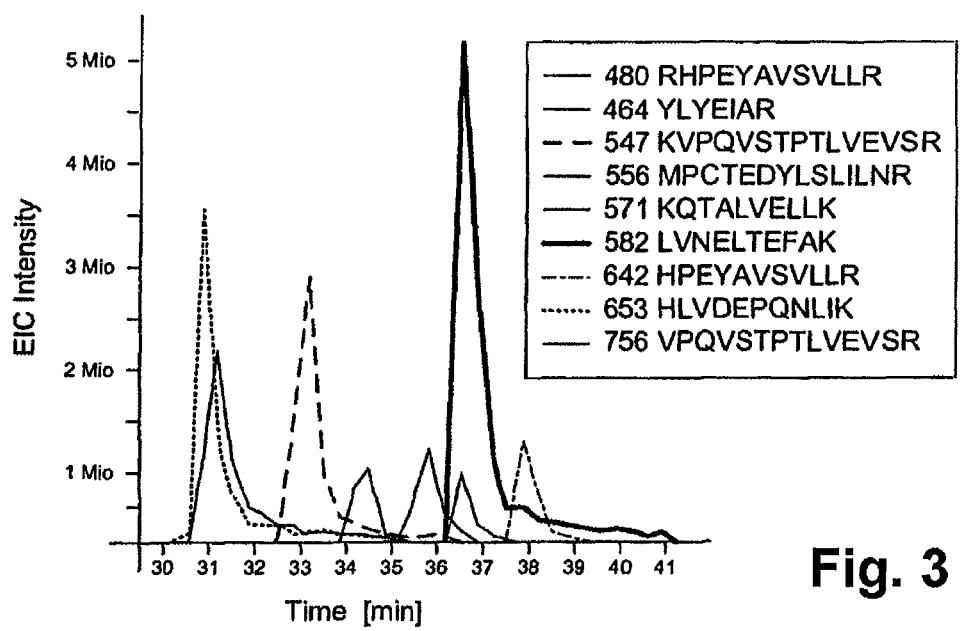

The measurement setup for the identification of peptide mixtures normally includes a separation system such as for example high-performance liquid chromatography (HPLC), which is coupled directly to a mass spectrometer (e.g. LTQ-FT). As a result, the various peptides enter the mass spectrometer in different time windows and can be analyzed (FIG. 3). Depending on the separation, the time windows in which the peptide is available can vary considerably and moreover they sometimes have large overlaps, leading to so-called time-critical measurements. Accordingly, for each peptide only a few measurements might be available, for identifying these unambiguously. This, and the fact that the prevailing concentrations of the peptides can also vary considerably, make it essential in a measuring experiment to decide at run time which measurements, and when, should be performed for a peptide.

However, such decisions can only be taken on the basis of evaluated mass spectra, as information about the completeness and uniqueness of the amino acid sequence belonging to the particular peptide can only be derived from these.

The measuring process of a mass spectrometer is at present controlled by predefinable measuring methods, which only operate dynamically to a limited extent and normally perform a rigid alternation between the previously defined measuring modes (for example MS, MSn). As an example, the flow chart of a widely used procedure is presented below, and is visualized in FIG. 4 on the basis of measured spectra:

Measuring Mode 1.
Recording of an overview spectrum with all ions that arise (MS)
Measuring Mode 2.
Fragmentation of the 1st most intense ion signal from overview spectrum (1) (MS2)
Measuring Mode 3.
Fragmentation of the 2nd most intense ion signal from overview spectrum (1) (MS2)
Measuring Mode 4.
Fragmentation of the 3rd most intense ion signal from overview spectrum (1) (MS2)
. . . Go to measuring mode 1.

Figure 4:
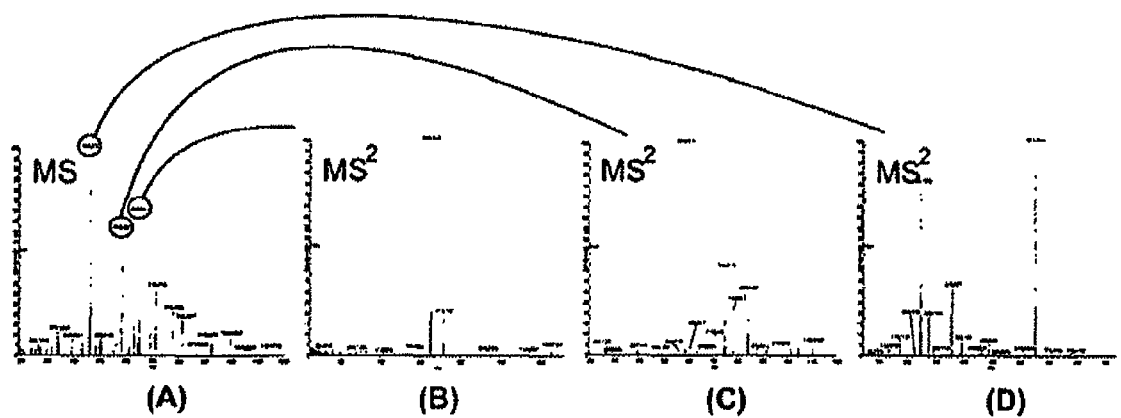

The measurement sequence shown as an extract in FIG. 4 is maintained throughout the separation run regardless of the fragmentation efficiency or extractable statements of the individual spectra. Such a procedure inevitably leads to data that are redundant and are unnecessary for a sequencing and moreover neglects peptides of low concentration with low intensities. The additional use of predefinable lists with preferred ion masses and those to be ruled out, and exclusion lists, which already exclude fragmented ions from further measurements during the measuring experiment, can only limit the amount of possible precursor ions.

Without information about the existing measurements (measurement data $d_1$, $d_2$, $d_3$) of the peptides and the associated conclusion (statements $a_1$, $a_2$, $a_3$) about completeness and uniqueness of the investigated amino acid sequences, at run time it is not possible to react optimally to the occurrence of various ions.

Based on the mass difference ($\Delta m$) between two peptide fragments of a fragment spectrum, it is possible to make out the quantity of possible amino acids (including their modifications), in which they differ.

The strategy of using a set of mass differences ($\Delta m$), in order to reveal the fragment series of a peptide, is called de-novo sequencing and assumes knowledge of the masses of all amino acids and with modified forms that are to be incorporated. If the observed fragment series of the investigated peptide are complete or overlap these sufficiently, the sequence of a peptide can be determined by successive aligning of fragments which in each case differ by just one amino acid (optionally including any modification) (cf. FIG. 2).

One difficulty in de-novo sequencing is incorporating all possible combinations of amino acids and their modified forms in the determination of the mass gap. The computational effort increases with the number of possible modifications so much (exponentially) that application at run time is not possible, especially in the case of time-critical measurements.

The invention described here solves this problem in that the necessary database 110 with all possible combinations of amino acids, including their possible modifications, is produced beforehand as mass-sequence pair. The resultant mass differences ($\Delta m$) can therefore be assigned to the possible amino acid forms by simple data requests.

This novel method makes it possible to evaluate the measured values of the fragment spectra through the speed advantage of data requests immediately, so that a selected ion (for example a peptide) is completely identifiable from the available measurement data. We call this method Online De-Novo Sequencing. Based on knowledge about partial identifications already achieved, the measurement parameters (device parameters $p_1$, $p_2$, $p_3$) of the mass spectrometer can be varied deliberately for the rest of the measurement. This feedback of the information obtained to the measuring process in progress permits, especially in the case of time-critical measurements (for example HPLC/MS), target-oriented intervention in the measuring process, while the ions to be investigated are still available.

The mass spectrometer (LTQ-FT) selected for this example of application produces, in pulsed cycles, mass spectra according to a measuring mode that is specified in advance in each case. The cycle time is on average about ~1 s. We regard this time window as a guide for the evaluation of a mass spectrum and feedback of the results obtained to the future measurements.

The following is a detailed account of the procedure (as sequence of individual steps)—which we call DBnovo hereinafter—for the evaluation of fragment spectra and is supported with the temporal extent of the partial processes determined in various tests for the purpose of classification/clarification of feasibility.

Step 01: Preparation of the Measured Values and Deconvolution

Figure 5:
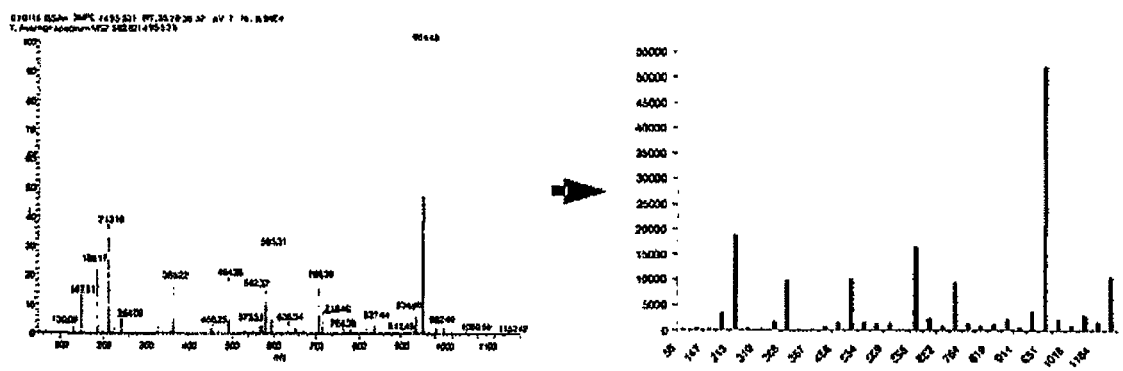

After deconvolution and filtering of the measurement data $d_1$, $d_2$, $d_3$ (peaks), the masses of the fragments occurring are determined and are prepared for further processing (cf. FIG. 5). During this, it is possible to vary the average number of signals per measurement, and determine signals with identical information content, the threshold value for signal-to-noise ratio (i.e. up to what value is a signal deemed to be usable, or is ascribed to the general noise of the measurement) or the like.

Step 02: Production of the Data Relations b1, b2, b3

Figure 6:
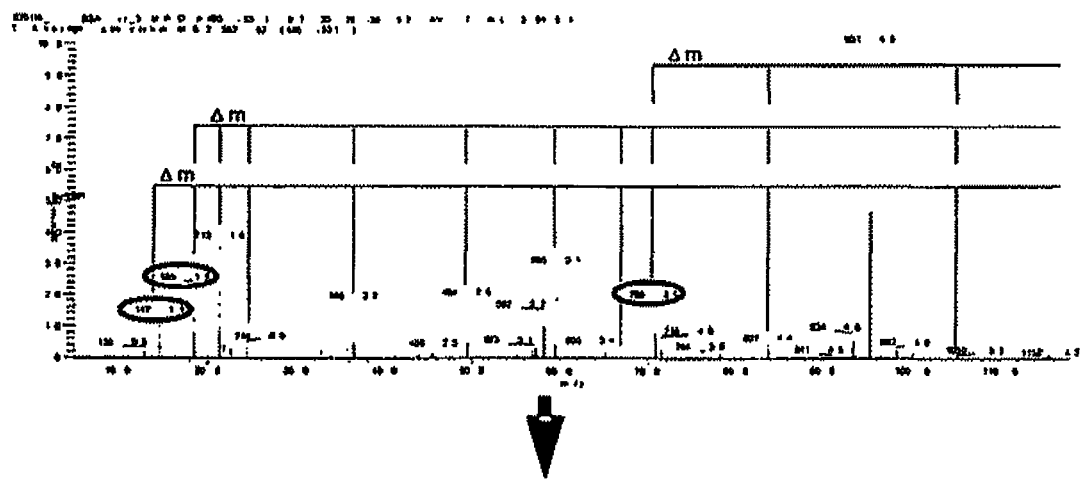
Figure 7A:
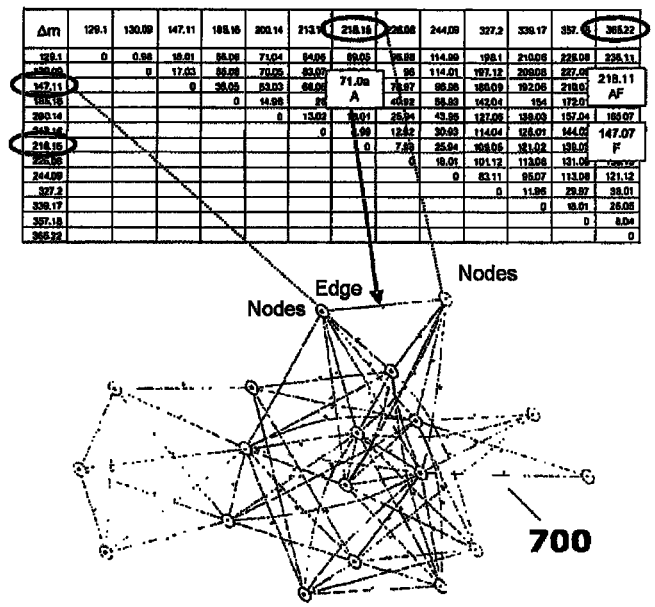
Figure 7B:
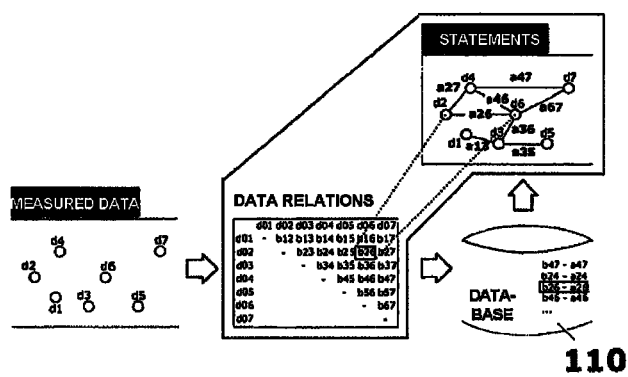

The extracted masses are related to one another (data relations $b_1$, $b_2$, $b_3$) by finding their mass differences ($\Delta m$) and presenting them in a $\Delta m$-matrix (cf. FIG. 6). It is possible to vary the number of signals to be compared, allowance for optimization quantities (e.g. prior elimination of duplicates) or the like.

Step 03: Evaluation of the Data Relations b1, b2, b3

For all masses of the fragment peptides of a fragment spectrum and the nonredundant set of mass differences of the associated $\Delta m$-matrix, a data request is sent to the previously produced database 110.

From the results of the data request, an undirected graph 700 is constructed (cf. FIG. 7). In this, a node is produced for each mass. All mass differences for which an entry exists in the database 110 are defined as edges between the associated nodes and are provided with the result of the inquiry. Nodes without relations are ignored. For evaluating the data relations b1, b2, b3, it is possible to vary the number of requested mass gaps per fragment spectrum (size of the matrix), the number of entries of the requested database, previous optimizations (for example elimination of unusable mass gaps (e.g. number of amino acid correspondences found is too large, so that no usable information can be obtained)) or the like.

Step 04: Derivation of Statements $a_1$, $a_2$, $a_3$

Figure 8:
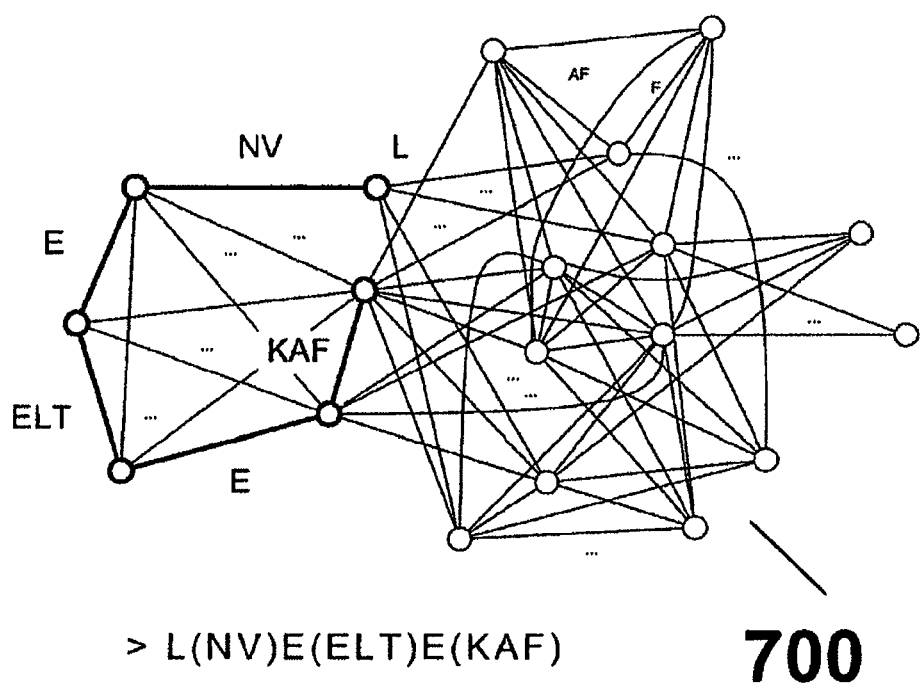

Statements $a_1$, $a_2$, $a_3$ are connected with the finding of paths through the graphs 700 produced in step 03 (cf. FIG. 8). In a typical embodiment, the node with the lowest mass forms the starting point. All paths that run along the edges to nodes in each case of higher mass are sought, until the node that represents the mass of the peptide is reached. The resultant paths correspond to possible parts of fragment series of the peptide investigated. (Alternatively it is also possible to search starting from the node with the highest mass. The algorithm is then modified correspondingly in an obvious manner, for example by going along the edges to nodes of lower mass in each case.)

If exclusively unambiguous amino acid forms can be assigned to the starting node and all edges, an unambiguous and complete fragment series is produced and consequently the sequence of the peptide. Nonunambiguous edges show, in contrast, sequence regions of the peptide which must be investigated further for identification in the subsequent measurements. During derivation of statements $a_1$, $a_2$, $a_3$ it is possible to vary the size (number of nodes) of the resultant graph, the degree of linkage and the unambiguity of the resultant graph, the completeness of the mass gaps found, or the like.

Step 05: Alignment of Statement $a_1$, $a_2$, $a_3$ and Setting the Target

From the derived statements $a_1$, $a_2$, $a_3$ of the preceding evaluation, i.e. the identification of the amino acid sequence of the investigated peptide achieved by online de-novo sequencing, it is established how completely and unambiguously the imposed (partial) target is reached. During this it is possible for example to vary the degree of sequence coverage or the like.

Step 06: Target-oriented Variation of the Device Parameters, Measuring Mode

From the previously derived statements $a_1$, $a_2$, $a_3$, the existing target coverage, and the peptide ions available in the course of the measurement, the device parameters $p_1$, $p_2$, $p_3$, and hence the subsequent course of measurement are determined target-oriented. During this it is possible for example to vary the present signal strength (variation of the signal in the chromatogram) or the like.

Figure 9:
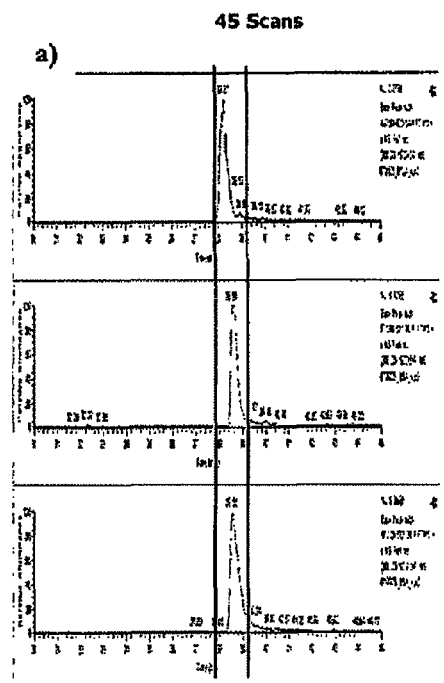

The invention is used especially advantageously for example in a time-critical HPLC/MS run. During an HPLC/MS test run (measuring experiment) various peptides of a starting mixture can enter the mass spectrometer simultaneously. The concentration of each peptide passes through a maximum caused by the separation system, until the peptide can no longer be detected (FIG. 9*a*). The superposition of individual concentration curves makes sequential measurement of the peptides difficult. It is therefore necessary to establish an order of priority, depending on the availability of a peptide. If the need for measurements for each peptide, to identify it unambiguously, is kept as small as possible, the total number of peptides that can be analyzed is increased.

Based on an HPLC/MS test run that had already been executed, each mass spectrum was analyzed for the extent to which the fragmentation of the peptide already carried out led to the identification. In this case it would have been possible to use each further measurement in the same measuring mode for the sequencing of additional peptides.

In the case of a nonunambiguous sequencing of a peptide, measurements with varied measuring mode on the corresponding peptide were used. In the case of complete and unambiguous sequencing or attainment of the maximum possible measurements, the fragmentation of the peptide was stopped and the (partial) sequence extracted to date and the increase in sequence coverage (compared with existing methods) was the output. This is shown in FIGS. 9*b-c* for the example of three peptides, which appear in a time window of about 1.5 min.

Another example is the evaluation of a fragment spectrum of an MeCAT-Lu modified peptide P3. IRMPD was used as the fragmentation method. Large parts of the sequence are not unambiguous (upper marking b series, lower marking y series).

According to a different measuring mode with ECD as fragmentation method, the substance was measured again and the resulting mass spectrum was evaluated. The peptide is now completely and unambiguously identified by an almost complete c series (upper markings) and some fragments of the z series (lower markings) except for the order of two amino acids on the N-terminus.

Tests with the existing, previously defined measuring methods have shown that the resultant mass spectra give rise to a pool of unnecessary measurements. This includes for example sets of identical measurements (redundant data), unnecessary measurements of a statement already known at the current time point and a set of unusable measurements. This results in measurements being "wasted" and part sequences possibly only being identified nonunambiguously and incompletely.

In comparison, the resultant mass spectra were first evaluated offline with DBnovo in the imposed time window (is), in order to show, by means of the resultant statements, the sequence regions of the peptides that are still required for complete sequence coverage.

By choosing a target-oriented altered measuring mode from a set of established basic modes, it was demonstrated that with repeat fragmentation of the total peptide (MS$^2$) or of a selected fragment (MS3), a complete and unambiguous sequencing could be achieved.

It is therefore possible, by use of the invention, to force the identification through situation-specific alteration of the measuring process and through recognition (of the existence) of a completely and unambiguously elucidated sequence, to direct the focus contemporaneously onto another peptide.

The invention is not restricted in its embodiment to the preferred examples presented above. Rather, a number of variants is conceivable, which make use of the arrangement according to the invention and the method according to the invention even with fundamentally different forms of execution.

The invention claimed is:

1. A method of analyzing biopolymers and/or derivatives thereof using a mass spectrometer system, comprising steps of:
providing a database including information about biopolymers and/or derivatives thereof in association with corresponding mass spectroscopy data and relations between or among items of the mass spectroscopy data, the database comprises at least one of mass differences between monomers and/or polymers of the biopolymers and intensity differences;
acquiring mass spectroscopy data using the mass spectrometer system, the mass spectroscopy data comprise at least one of mass/charge ratios, signal intensities, physical quantities, and quantities derivable therefrom;
evaluating the acquired mass spectroscopy data to derive relations between or among items of the acquired mass spectroscopy data;
making at least one inquiry to the database having criteria based on at least one of the acquired mass spectroscopy data and the relations between or among items of the acquired mass spectroscopy data and retrieving information from the database about the biopolymers and/or derivatives thereof, the information including candidates for unelucidated parts of a sequence of at least one of the biopolymers and/or derivatives thereof; and in accordance with the retrieved information about acquired measurement objects, determining precursors for further fragmentations, selecting fragmentation methods, and adjusting fragmentation parameters to the determined unelucidated sequence parts;
fragmenting the determined precursors according to the selected fragmentation methods and the selected fragmentation parameters;
acquiring mass spectroscopy data for the resulting fragments; and
determining at least a portion of the sequence for unelucidated parts of the sequence of at least one of the biopolymers and/or derivatives thereof.

2. The method as claimed in claim 1, wherein
the biopolymers and/or their derivatives being built up from monomers, and a subunit of a biopolymer and/or of a derivative, which comprises several monomers, forms a polymer.

3. The method as claimed in claim 1, wherein the biopolymers or derivatives also comprise modified biopolymers or modified derivatives.

4. The method as claimed in claim 1, wherein the monomers also comprise modified monomers.

5. The method as claimed in claim 1, wherein the biopolymers or derivatives are proteins, peptides, DNA, RNA, PNA, LNA, TNA, GNA, polysaccharides, lipids, polyglucosamines, polyhydroxyalkanoates, cutin, suberin or lignin or combinations thereof.

6. The method as claimed in claim 1, wherein the database comprises at least on of: previously calculated measurement data, relations between or among the previously calculated measurement data, information about physical and/or chemical properties of the measurement objects, and information derived from preceding measurements.

7. The method as claimed in claim 2, wherein the database comprises at least one of mass differences between monomers and/or polymers of the biopolymers and intensity differences.

8. The method as claimed in claim 7, wherein the database comprises mass differences between polymers with distances apart of one or more monomers.

9. The method as claimed in claim 1, wherein the step of making at least one inquiry to the database includes determining elucidated parts of a sequence of at least one of the biopolymers.

10. The method as claimed in claim 9, wherein determined elucidated sequence parts are combined with sequence parts obtained in other measurements to determine the completeness of the degree of sequencing.

11. The method as claimed in claim 9, wherein an assignment to a biopolymer group is derived from determined elucidated sequence parts.

12. The method as claimed in claim 1, wherein the at least one inquiry to the database includes criteria based on the masses and mass differences in a fragment spectrum.

13. The method as claimed in claim 1, wherein from the results of the database inquiry, two masses of biopolymer fragments are assigned to each other and corresponding information on assignment is produced, when at least one entry that corresponds to a mass difference between these two masses is found in the database.

14. The method as claimed in claim 2, wherein the information on assignment further comprises information about one or more monomers, which represent the mass difference between the two masses.

15. The method as claimed in claim 2, wherein the determination of candidates for the unelucidated parts of the sequences of biopolymers includes the application of at least one of methods of graph theory, methods of artificial intelligence, methods for using neural networks, genetic algorithms, and evolution strategies.

16. The method as claimed in claim 2, wherein by evaluating the masses assigned to each other or information on assignment, possible candidates for unelucidated parts of the sequence of the biopolymers are determined, in which at least one linking chain is determined between masses, starting from one mass, which comprises elements to which in each case a mass is assigned, and linkages, to which in each case information about one or more monomers is assigned, which represent the mass difference between the two linked masses, with the at least one linking chain always running in each case in the direction of increasing or decreasing masses, and with possible candidates for unelucidated sequence parts of the biopolymers being indicated by linkages, to which at least two monomers are assigned.

17. The method as claimed in claim 11, further comprising identifying the presence of unelucidated sequence parts by applying at least one of the following criteria: linkages exist, to which at least two monomers are assigned and the lowest mass does not correspond to the mass of an individual monomer, or linkages exist, of the highest mass to the mass of the unfragmented biopolymers, to which at least two monomers are assigned, and the complete elucidation of a sequence is indicated by a linking chain, which consists exclusively of monomers.

18. The method as claimed in claim 1, wherein the measuring system is controlled in such a way that, in relation to the information about acquired measurement objects from a first measuring operation during the measuring experiment, the measuring operation directly following the first measuring operation or a later measuring operation is parameterized.

19. The method as claimed in claim 18, wherein the parameters for a measuring operation during the measuring experiment are selected according to a task list.

20. The method as claimed in claim 1, wherein at least one device parameter of the measuring instrument is varied depending on the candidates determined for unelucidated parts of a sequence of a biopolymer.

21. The method as claimed in claim 20, wherein the variation of the at least one device parameter takes place according to whether the signal representing the unelucidated sequence part is still present.

22. The method as claimed in claim 1, characterized in that at least one device parameter is varied by establishing the device parameters of the next measurement on the basis of the current measurement.

23. The method as claimed in claim 2, wherein the determination of unelucidated sequence parts and the determining precursors, selecting fragmentation methods, and adjusting fragmentation parameters essentially take place in real time during the measuring operation.

24. A mass spectrometer system comprising:
a database including information about biopolymers and/or derivatives thereof in association with corresponding mass spectroscopy data and relations between or among items of the mass spectroscopy data, the database comprises at least one of mass differences between monomers and/or polymers of the biopolymers and/or derivatives thereof and intensity differences;
at least one mass spectrometer for acquiring mass spectroscopy data, the mass spectroscopy data comprise at least one of mass/charge ratios, signal intensities, physical quantities, and quantities derivable therefrom;
a computer readable storage medium having program instructions for performing steps of:
evaluating the acquired mass spectroscopy data to derive relations between or among items of the acquired mass spectroscopy data;
making at least one inquiry to the database having criteria based on at least one of the acquired mass spectroscopy data and the relations between or among items of the acquired mass spectroscopy data and retrieving information from the database about the biopolymers and/or derivatives thereof, the information including candidates for unelucidated parts of a sequence of at least one of the biopolymers and/or derivatives thereof;
in accordance with the retrieved information about biopolymers and/or derivatives thereof, determining precursors for further fragmentations, selecting methods, and adjusting fragmentation parameters to the determined unelucidated sequence parts;
fragmenting the determined precursors using the selected fragmentation methods and adjusted fragmentation parameters;
acquiring mass spectroscopy data for the resulting fragments; and determining at least a portion of the sequence for the unelucidated parts of the sequence of the at least one of the biopolymers and/or derivatives thereof.

* * * * *

UNITED STATES PATENT AND TRADEMARK OFFICE
CERTIFICATE OF CORRECTION

PATENT NO. : 9,818,588 B2
APPLICATION NO. : 12/989951
DATED : November 14, 2017
INVENTOR(S) : Andreas Kuehn et al.

It is certified that error appears in the above-identified patent and that said Letters Patent is hereby corrected as shown below:

In the Claims

Claim 6, Column 21, Line 5:
Replace "comprises at least on of"
With --comprises at least one of--

Claim 12, Column 21, Line 30:
Replace "mass differences in a fragment sprectrum"
With --mass differences in a fragment spectrum--

Signed and Sealed this
Twenty-eighth Day of May, 2019

Andrei Iancu
*Director of the United States Patent and Trademark Office*